US012103899B2

(12) United States Patent
Kim et al.

(10) Patent No.: US 12,103,899 B2
(45) Date of Patent: Oct. 1, 2024

(54) METHOD FOR NON-OXIDATIVE DIRECT CONVERSION OF METHANE

(71) Applicant: KOREA RESEARCH INSTITUTE OF CHEMICAL TECHNOLOGY, Daejeon (KR)

(72) Inventors: Yong Tae Kim, Daejeon (KR); Sung Woo Lee, Daejeon (KR); Seok Ki Kim, Suwon (KR); Jungho Shin, Daejeon (KR); Seung Ju Han, Daejeon (KR); Hyun Woo Kim, Gwangju (KR); Eun Hae Sim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 48 days.

(21) Appl. No.: 18/025,372

(22) PCT Filed: Aug. 10, 2021

(86) PCT No.: PCT/KR2021/010582
§ 371 (c)(1),
(2) Date: Mar. 8, 2023

(87) PCT Pub. No.: WO2022/080638
PCT Pub. Date: Apr. 21, 2022

(65) Prior Publication Data
US 2023/0331644 A1 Oct. 19, 2023

(30) Foreign Application Priority Data
Oct. 12, 2020 (KR) .......................... 10-2020-0130992

(51) Int. Cl.
*C07C 2/76* (2006.01)

(52) U.S. Cl.
CPC ............ *C07C 2/76* (2013.01); *C07C 2521/18* (2013.01); *C07C 2523/26* (2013.01); *C07C 2523/755* (2013.01)

(58) Field of Classification Search
CPC ... C07C 2/76; C07C 2521/18; C07C 2523/26; C07C 2523/755; C07C 1/02; C07C 9/06;
(Continued)

(56) References Cited

U.S. PATENT DOCUMENTS

2007/0100190 A1* 5/2007 Cimino ................ B01J 23/6562
585/658
2014/0336432 A1 11/2014 Bao et al.
(Continued)

FOREIGN PATENT DOCUMENTS

| KR | 10-2017-0099592 A | 9/2017 |
| KR | 10-2018-0077399 A | 7/2018 |
| KR | 10-2020-0095071 A | 8/2020 |

OTHER PUBLICATIONS

International Search Report issued on Nov. 26, 2021, for corresponding International Application No. PCT/KR2021/010582, 6 pages, with English machine translation.
(Continued)

*Primary Examiner* — Ali Z Fadhel
(74) *Attorney, Agent, or Firm* — Hauptman Ham, LLP

(57) ABSTRACT

The present disclosure relates to a method for non-oxidative direct conversion of methane. Specifically, in the method, a methane/hydrogen gas is introduced into an Inconel 600 reactor at a superficial velocity of 100 to 200 cm·min$^{-1}$ and a catalyst is not externally introduced into the reactor. Under the conditions, a non-oxidative direct methane conversion reaction is performed in the Inconel 600 reactor. The method
(Continued)

maximizes the reaction rate, minimizes coke formation, and increases the yields of $C_2$ hydrocarbon compounds and aromatic compounds.

11 Claims, 5 Drawing Sheets

(58) Field of Classification Search
CPC ......... C07C 11/04; C07C 11/24; C07C 13/47; C07C 15/04; C07C 15/06; C07C 2523/745
See application file for complete search history.

(56) References Cited

U.S. PATENT DOCUMENTS

| | | | |
|---|---|---|---|
| 2016/0016862 A1* | 1/2016 | Noyes | B01J 8/1836 422/187 |
| 2016/0362351 A1* | 12/2016 | Nagaki | B01J 23/745 |

OTHER PUBLICATIONS

Written Opinion issued on Nov. 26, 2021, for corresponding International Patent Application No. PCT/KR2021/010582, 4 pages.

Razdan et al., "Influence of ethylene and acetylene on the rate and reversibility of methane dehydroaromatization on Mo/H-ZSM-5 catalysts," Journal of Catalysis, Nov. 27, 2019, vol. 381, pp. 261-270; Cited in NPL Nos. 1 and 2.

Xu et al., "Effect of superficial velocity on the coking behavior of a nanozeolite-based Mo/HZSM-5 catalyst in the non-oxidative CH4 dehydroaromatization at 1073 K," Catalysis Science & Technology, Jul. 31, 2013, 9 pages; Cited in NPL Nos. 1 and 2.

Korea Research Institute of Chemical Technology, "Development of Catalyst Design Technology for Non-Oxidative Direct Conversion of Methane for Production of Light Olefins and Aromatics," Climate Change Response Technology Development Final Report, Ministry of Science and ICT, Oct. 2017, 80 pages; With English abstract; Cited in NPL Nos. 1 and 2.

* cited by examiner (a)

(b)

METHOD FOR NON-OXIDATIVE DIRECT CONVERSION OF METHANE

CROSS-REFERENCE TO RELATED APPLICATION

The present application is a national stage filing under 35 U.S.C § 371 of PCT application number PCT/KR2021/010582 filed on Aug. 10, 2021, which is based upon and claims the benefit of priorities to Korean Patent Application No. 10-2020-0130992, filed on Oct. 12, 2020, in the Korean Intellectual Property Office. All of the aforementioned applications are hereby incorporated by reference in their entireties.

TECHNICAL FIELD

The present disclosure relates to a non-oxidative direct methane conversion method. More particularly, the present disclosure relates to a method of producing hydrocarbon compounds including $C_2$ compounds and aromatic compounds through a direct conversion reaction of methane, which is a major component of natural gas, under an oxygen-free atmosphere.

BACKGROUND ART

Recently, efforts have been made to convert methane ($CH_4$), which can be obtained from natural gas, shale gas, etc., into high value-added products such as transportation fuels or expensive chemicals. Representative examples of value-added products obtained from methane are light olefins (ethylene, propylene, and butylene). Currently, the methanol to olefins (MTO) route and the Fischer-Tropsch to olefins (FTO) route are the most feasible routes to obtain olefins from methane. The MTO technology produces light olefins via methanol synthesis from synthetic gas ($H_2$+CO) obtained through methane reforming, and the FTO technology directly produces light olefins from synthetic gas. The technique of producing high value-added products via synthetic gas has problems in that a synthetic gas production stage suffers low energy efficiency, and $H_2$ or CO is required to remove O atoms from CO molecules of the synthetic gas, which results in a decrease in the utilization efficiency of H or C atoms throughout the whole process.

Therefore, new technology for directly converting methane into high value-added products without involving synthetic gas production is required. For direct conversion of methane into a high value-added product, it is first necessary to activate methane by breaking strong C—H bonds (434 kJ/mol). Given the requirements, there has been active research on the oxidative methane coupling technology, which uses oxygen to activate methane.

As a related art concerning a non-oxidative methane conversion reaction, Korean Patent Application Publication No. 2017-0099592 discloses a method of performing oxidative coupling of methane in a reactor having a porous electrode active layer containing an Inconel alloy and a composite material of a spinel-structure oxide and an ion-conductive fluorite-structure oxide.

However, in the OCM reaction, $H_2O$ and $CO_2$, which are thermodynamically stable, are formed in large quantities due to the high reactivity of $O_2$, so the utilization efficiency of H or C atoms is problematic.

To solve this problem, a technique of preparing ethylene, aromatic compounds, etc. by direct conversion of methane under anaerobic or anaerobic conditions has been recently developed. However, due to the low reactivity of methane in the process of conversion into hydrocarbons, the process needs to be performed at high temperatures and low pressures, and the development of a suitable catalyst is essential. However, research has shown that the problem of rapid catalyst deactivation due to carbon deposition (called coke deposition) under conditions of high temperature and low pressure is a concerning issue (see Non-Patent Documents 0001 and 0002).

Accordingly, U.S. Publication No. 2014-0336432 discloses a non-oxidative methane conversion method in which, to inhibit the deposition of carbon (coke) under high-temperature and atmospheric-pressure conditions, a methane-containing material is reacted in the presence of a catalyst made of a metal provided as a dopant in the lattice of molten amorphous silicon (Si) bound to at least one of C, N, and O.

Although the document discloses a catalyst for suppressing coke formation and increasing catalytic reaction rate compared to existing catalysts produced by a sol-gel process or a precipitation process and used for non-oxidative direct conversion of methane, the catalyst has a problem in that the selectivity of coke increases with increasing conversion rate of methane, resulting in deterioration in the selectivity and production rate of hydrocarbon compounds.

On the other hand, in the process of preparing ethylene and aromatic compounds from methane, the main factors causing coke formation include the surface of a catalyst cluster charged in a reactor, the stagnant flow of fluid, the material of the reactor, the surface roughness of the reactor, etc. The non-oxidative conversion reaction of methane is expected to be improved by controlling these factors.

Accordingly, the present disclosure has been made to propose a technique of improving the conversion rate of methane and the production rate of hydrocarbon compounds such as ethylene and benzene by using an Inconel 600 reactor. The reactor improves the methane conversion rate by improving the flow of fluid and the superficial velocity and weight hourly space velocity which are factors indicating the contact between the fluid and a catalyst, thereby improving the conversion rate of methane. In addition, the reactor suppresses coke formation, thereby increasing the production rate of hydrocarbon compounds.

DISCLOSURE

Technical Problem

The present disclosure has been made in view of the problems occurring in the related art, and an objective of the present disclosure is to provide a non-oxidative direction methane conversion method in which a direct methane conversion reaction is performed in an Inconel 600 reactor without additional feeding of a direct methane conversion catalyst to the Inconel 600 reactor. The method maximizes a catalytic reaction rate, minimizes coke formation, and maximizes the production rates of $C_2$ hydrocarbons and aromatic compounds.

Technical Solution

In order to achieve the objective, in one aspect of the present disclosure, there is provided a non-oxidative direct methane conversion method including: (a) supplying a methane feed gas comprising methane at a superficial velocity in a range of 100 cm·min$^{-1}$ to 200 cm·min$^{-1}$ to a reactor having an inner surface of made of Inconel 600; and (b)

obtaining a compound having two or more carbon atoms, produced in the reactor having the inner surface made of Inconel 600.

In a preferred embodiment of the present disclosure, the methane feed gas may be supplied at a weight hourly space velocity in a range of 8 $min^{-1}$ to 10.5 $min^{-1}$.

In another preferred embodiment of the present disclosure, the methane feed gas may be supplied at a flow rate in a range of 80 $cm^3 \cdot min^{-1}$ to 300 $cm \cdot min^{-1}$.

In a further preferred embodiment of the present disclosure, methane may be contained in the methane feed gas in a volume ratio in a range of 20% to 100% with respect to the volume of the methane feed gas.

In a further preferred embodiment of the present disclosure, the methane feed gas may contain methane and hydrogen.

In a further preferred embodiment of the present disclosure, the non-oxidative direct conversion reaction temperature of the methane feed gas is in a range of 1000° C. to 1250° C.

In a further preferred embodiment of the present disclosure, the ratio of amorphous carbon and crystalline carbon in a carbon layer formed in the Inconel 600 reactor may be in a range of 1:4 to 2:3.

According to another aspect of the present disclosure, there is provided a catalyst for non-oxidative direct conversion of methane, the catalyst being a composite catalyst system including Inconel 600 coated with a carbon layer in which as carbon components, amorphous carbon and crystalline carbon are present in a ratio of 1:4 to 2:3.

Advantageous Effects

The non-oxidative direct methane conversion method according to the present disclosure has the advantages of: maximizing the catalytic reaction rate in an Inconel 600 reactor without additionally providing a non-oxidative direct methane conversion catalyst into the Inconel 600 reactor; minimizing the generation of crystalline coke; and maximizing the production rate of $C_2$ hydrocarbon compounds and aromatic compounds.

BEST MODE

Figure 1:
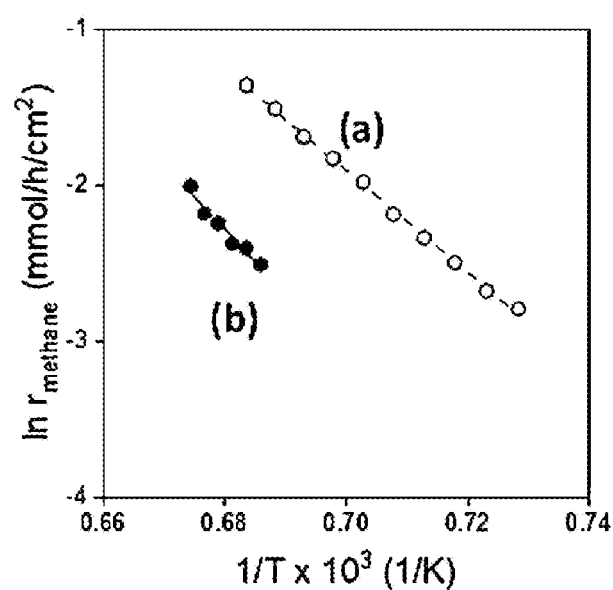
In FIG. 1, (a) and (b) are graphs illustrating the results of comparison in apparent activation energy Ea of methane in non-oxidative direct methane conversion reactions performed according to Example 1 of the present disclosure and Comparative Example 1, respectively.
Figure 1:
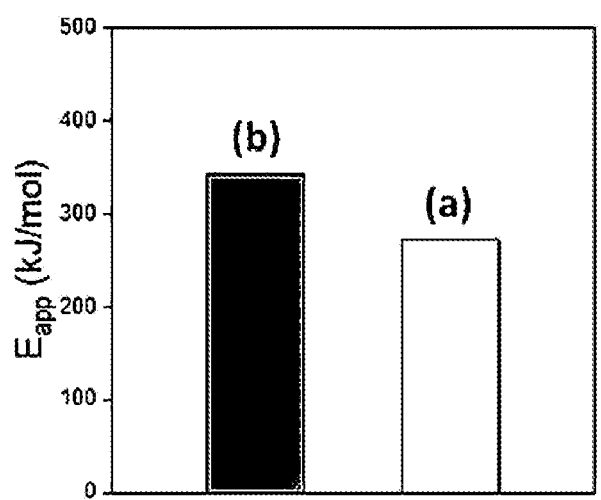

Unless otherwise defined, all terms including technical and scientific terms used herein have the same meaning as commonly understood by those who are ordinarily skilled in the art to which this disclosure belongs. In general, the nomenclature used herein is well-known and commonly used in the art.

It will be further understood that the terms "comprises", "includes", or "has", when used in this specification, specify the presence of an element, but do not preclude the presence or addition of one or more other elements unless the context clearly indicates otherwise.

In one aspect, the present disclosure provides a non-oxidative direct methane conversion method including: (a) supplying a methane feed gas containing methane at a superficial velocity in a range of 100 $cm \cdot min^{-1}$ to 200 $cm \cdot min^{-1}$ into an Inconel 600 reactor; and (b) obtaining a $C_2$ or higher chemical compound produced in the Inconel 600 reactor.

More specifically, in the non-oxidative direct methane conversion method according to the present disclosure, since the methane feed gas including methane is introduced into the Inconel 600 reactor at a superficial velocity in a range of 100 $cm \cdot min^{-1}$ to 200 $cm \cdot min^{-1}$, there are advantages that the catalytic reaction rate is maximized, coke formation is minimized, and the conversion rates into $C_2$ hydrocarbon compounds and aromatic compounds from methane are considerably high.

Hereinafter, the non-oxidative direct conversion method of methane, according to the present disclosure, will be described in greater detail.

The Inconel 600 reactor refers to a reactor made of a metal alloy including: as main components, about 72% of nickel, about 14% to 17% of chromium, and about 6% to 10% of iron; and as auxiliary components, up to 0.14% of carbon, up to 1.0% of manganese, up to 0.015% of sulfur, up to 0.5% of silicon, and up to 0.5% of copper. The Inconel 600 reactor serves as a precursor of a non-oxidative direct methane conversion catalyst as well as provides a reaction zone for the non-oxidative direct conversion of methane.

A methane feed gas including a methane gas and an inert and/or non-inert gas is introduced into the Inconel 600 reactor, and reactions occur at a high temperature in the Inconel 600 reactor without additionally feeding a catalyst into the reactor. During the reaction, a carbon catalyst useful for production of $C_2$ hydrocarbon compounds and aromatic compounds is synthesized on the inner surface of the reactor.

In addition to the Inconel 600 reactor providing a reaction zone, a reaction apparatus further includes other components and accessories such as supply pipes, gas exhaust pipes, product discharge pipes, and a heating member. The reaction apparatus may further include one or more instruments for measurement. The one or more measurement instruments may be any suitable measurement instruments known to the ordinarily skilled in the art. Specifically, the instruments may include pressure indicators, pressure transmitters, thermowells, temperature-display regulators, gas sensors, analyzers, and viscometers. The components and accessories may be connected to the reactor at various positions.

The non-oxidative direct conversion reaction of methane is performed at a superficial velocity in a range of 100 cm·min$^{-1}$ to 200 cm·min$^{-1}$, which improves the conversion rate of methane and the production rates of $C_2$ hydrocarbon and aromatic compounds. That is, a high molecular weight carbon layer is formed on the inner surface of the Inconel 600 reactor. A portion of the metal components in the Inconel 600 is revealed onto the carbon layer, thereby maximizing the catalytic reaction rate and suppressing the formation of crystalline coke caused by adsorption of reactants on the surface of the Inconel 600 reactor.

Specifically, when the superficial velocity of the methane feed gas is lower than 100 cm·min$^{-1}$, the primary products (acetylene, ethylene, and benzene) may further undergo a condensation reaction through a gas phase reaction in the reactor, thereby accelerating the production of coke particles. When the superficial velocity of the methane feed gas exceeds 200 cm·min$^{-1}$, the activation energy for methane conversion is significantly increased, and a crystalline carbon layer is formed on the inner surface of the Inconel 600 reactor. When cracks occur in the crystalline carbon layer, the precipitation of metal elements occurs on the surface of the Inconel 600 reactor, at a position exposed the internal environment of the reactor through the cracks. That is, metal particles such as iron particles are generated on the surface of the reactor, which promotes the formation of coke particles.

In addition, the weight hourly weight hourly space velocity (WHSV) of the methane feed gas supplied to the Inconel 600 reactor is preferably in the range of from 8 min$^{-1}$ to 10.5 min$^{-1}$. Specifically, when the weight hourly space velocity of the methane feed gas is lower than 8 min$^{-1}$, the formation of coke particles is promoted. When the weight hourly space velocity exceeds 10.5 cm·min$^{-1}$, a crystalline carbon layer is formed on the inner surface of the Inconel 600 reactor as with the case where the superficial velocity is excessively high. When cracks occur in the crystalline carbon layer, the precipitation of metal elements occurs on the surface of the Inconel 600 reactor at a position exposed the internal environment of the reactor through the cracks. That is, metal particles such as iron particles are generated on the surface of the reactor, which promotes the formation of coke particles.

The initial flow rate of the methane feed gas is in a range of 80 cm$^3$ min$^{-1}$ to 300 cm$^3$ min$^{-1}$ to induce a sufficient reaction to form a uniform high molecular carbon layer on the surface of the Inconel 600 reactor. When the flow rate is lower than 80 cm$^3$ min$^{-1}$, the retention time of the reactants in the gas phase in the reactor increases, which promotes the formation of coke particles through condensation. When the flow rate exceeds 300 cm$^3$ min$^{-1}$, the formation of the high molecular weight carbon layer on the surface of the Inconel 600 reactor is uneven.

The methane feed gas may include an inert and/or non-inert gas as well as methane gas. The inert gas and the non-inert gas serve to cause and maintain a stable reaction state. The inert gas may be nitrogen, helium, neon, argon, or krypton. The non-inert gas may be air, carbon monoxide, hydrogen, carbon dioxide, water, monovalent alcohols ($C_1$ to $C_5$), bivalent alcohols ($C_2$ to $C_5$), and alkanes ($C_2$ to $C_8$). Preferably, the inert gas and the non-inert gas may be argon and hydrogen.

The methane content may be in the range of from 20% to 100% by volume or more preferably in the range of 20% to 50% by volume with respect to the volume of the methane feed gas introduced into the reactor. The content of the inert and/or non-inert gas may be 50% by volume or more, and more preferably 80% by volume, with respect to the volume of the methane feed gas.

The non-inert gas in the methane feed gas may be hydrogen gas. In this case, the methane content may be in the range of from 0% to 80% by volume based on the volume of the methane feed gas, and more preferably in the range of from 50% to 80% by volume. By the non-oxidative direct conversion of methane, hydrogen can be produced as a reaction product as well as hydrocarbons (in this case, the volume ratio of ethylene:hydrogen=1:2). When the volume ratio of hydrogen is 50% or less, when the reaction proceeds along the axial direction of a tubular reactor, the concentration of hydrogen in the reactor gradually increases toward the tail end of the reactor, which has an advantage of suppressing a secondary reaction. However, the increasing concentration of hydrogen toward the tail end of the reactor may lead to poor uniformity in the thickness of a high molecular weight carbon layer formed on the surface of the reactor, resulting in increase in selectivity of coke particles. In addition, when the volume ratio of hydrogen gas is higher than 80%, there are problems in that a crystalline carbon layer rather than a high molecular weight carbon layer is formed, and may occur, and the reactivity of methane is reduced.

The reaction temperature may be in the range of from 1,000° C. to 1,350° C. and specifically in the range of from 1,000° C. to 1250° C. This temperature range is set in consideration of the selectivity and yield of hydrocarbons. This temperature ranges has an advantage of increasing the methane selectivity toward hydrocarbons. When the reaction temperature is lower than 1,000° C., the radical generation rate is low due to the methane activation, resulting in low energy efficiency. When the reaction temperature exceeds 1,350° C., there is a problem in that the retention time of methane in the reactor needs to be minimized to suppress the coke formation. In this case, the use of a tubular reactor is not suitable.

In the present disclosure, the reaction pressure is in the range of from 0.5 bar to 10 bar, and preferably in the range of from 0.5 bar to 5 bar. When the reaction pressure is lower than 0.5 bar, the formation of coke particles can be suppressed, but the energy efficiency is low due to the poor activation of methane. When the reaction pressure exceeds 10 bar, since the formation of coke particles is promoted, there is a problem in which the retention time in the reactor and the cooling of the reaction products must be effectively designed. That is, under the above-mentioned conditions, the formation of coke particles is minimized. As a result, during the reaction, the pressure drop attributable to the generation of coke particles is minimized, and the carbon efficiency attributable to the generation of coke particles is minimized.

In the non-oxidative direct methane conversion method according to the present disclosure, the ratio of amorphous carbon and crystalline carbon in the carbon layer formed on the surface of the Inconel 600 reactor is in the range of 1:4 to 2:3. The amorphous carbon covers with a uniform thickness of the carbon layer on the surface of the Inconel 600 and prevents cracks in the carbon layer, thereby suppressing the precipitation of metals in a high-temperature reduction environment. When a large amount of crystalline carbon is present on the surface of the carbon layer, there are problems in that surface cracks occur, the hardness of the reactor increases, and the precipitation of metal elements occurs.

As such, the products produced by the non-oxidative direct conversion of methane may include: hydrocarbons including alkynes, olefins, and paraffins such as ethane, ethylene, acetylene, propylene, and butylene; and benzene, toluene, xylene, ethylbenzene, naphthalene aromatic compounds. For the yield of each of the products obtainable by the non-oxidative direct methane conversion method according to the present disclosure, $C_2$ hydrocarbon compounds including ethane, ethylene, and acetylene and aromatic compounds are produced at high yields.

In addition, the present disclosure provides a catalyst for non-oxidative direct conversion of methane. The catalyst includes, as a composite catalyst component, a coated carbon layer and metal elements originating in Inconel 600. In the carbon layer, as the carbon component, amorphous carbon and crystalline carbon are present in a ratio in a range of 1:4 to 2:3.

In addition, the present disclosure provides a non-oxidative direct methane conversion method includes: a step of supplying a methane feed gas including methane gas and hydrogen gas into an Inconel 600 reactor having an inner surface on which a non-oxidative direct methane conversion catalyst is formed, the catalyst comprising a coated carbon layer and metal elements originating in Inconel 600 as a composite catalyst component, the carbon layer including amorphous carbon and crystalline carbon in a rate of 1:4 to 2:3; and producing compounds having two or more carbon atoms in the Inconel 600 reactor.

Specifically, the methane feed gas is supplied preferably at a superficial velocity in a range of 100 cm·min$^{-1}$ to 200 cm·min$^{-1}$. The supply of the methane feed gas at a superficial velocity range of 100 cm·min$^{-1}$ to 200 cm·min$^{-1}$ provides the advantages of maximizing the catalytic reaction rate, minimizing coke formation, and increasing the conversion rates of methane into $C_2$ hydrocarbon compounds and aromatic compounds.

In addition, the weight hourly space velocity of the methane feed gas is preferably in a range of 8 to 10.5 min$^{-1}$. The supply of the methane feed gas at a weight hourly space velocity of 8 to 10.5 min$^{-1}$ provides the advantage of suppressing the formation of crystalline coke particles and the generation of metal particles.

The present disclosure will be described in more detail with reference to examples described below. The examples described below are presented only to help understanding of the present disclosure, and the scope of the present disclosure is not limited thereto.

[Example 1] Non-Oxidative Direct Conversion Reaction of Methane

Direct conversion of methane was performed by feeding into an Inconel 600 reactor, methane and hydrogen at a volume ratio of 1:4.4. The superficial velocity of the gas was 133 cm·min$^{-1}$, the weight hourly space velocity of the gas was 8.9 min$^{-1}$, the gas retention time (gas phase) was 0.112 min, the reaction temperature was in the range of from 1110° C. to 1140° C., the reaction pressure $P_{total}$ was 1 bar, and the methane pressure $P_{CH4}$ was 0.44 bar.

[Comparative Example 1] Non-Oxidative Direct Conversion Reaction of Methane

Direct conversion of methane was performed by feeding into an Inconel 600 reactor, methane and hydrogen at a volume ratio of 1:4.4. The superficial velocity of the gas was 578 cm·min$^{-1}$, the weight hourly space velocity of the gas was 12.8 min$^{-1}$, the gas retention time (gas phase) was 0.078 min, the reaction temperature was in the range of from 1100° C. to 1190° C., the reaction pressure $P_{total}$ was 1 bar, and the methane pressure $P_{CH4}$ was 0.44 bar.

[Experimental Example 1] Non-Oxidative Direct Conversion Reaction Rate of Methane After the completion of the reactions of Example 1 and Comparative Example 1, the obtained gas-phase hydrocarbons were analyzed by gas chromatography using the Series 6500 manufactured by YL Instrument Co., Ltd. The products in gas phase were analyzed using a thermal conductivity detector (TCD) connected to a column called ShinCarbon ST (Restek Corp., Catalog No. 80486-800) and two flame ionization detectors (FID) connected to two columns called Rt-alumina bond/Na$_2$SO$_4$ (Restek Corp., Catalog No. 19756) and RTx-VMS (Restek Corp., Catalog No. 49915). $H_2$, $CH_4$, Ar, $C_2H_6$, $C_2H_4$, and $C_2H_2$ in the product gas were separated by ShinCarbon ST column and detected by the TCD. The conversion rate was determined by the ratio of the area of $CH_4$ to the area of Ar, according to the international standard. $C_2$ products were separated through the ShinCarbon ST column and the Rt-alumina bond/Na$_2$SO$_4$ column and detected by the TCD and FID. Light hydrocarbons in the range of $C_3$ to $C_5$ were separated by the Rt-alumina BOND column and detected by the FID, and aromatic compounds including benzene were separated by the RTx-VMS column and detected by the FID. All gases were quantified using standard samples. The coke selectivity was calculated according to the equation "Scoke=100–ΣProduct Selectivity". The methane conversion rate was converted to the reaction rate at a given reaction temperature. The variables in the Arrheius Formula were substituted with the calculated values to obtain the apparent activation energy (Ea). The results are shown in FIGS. 1 and 2.

Figure 2:
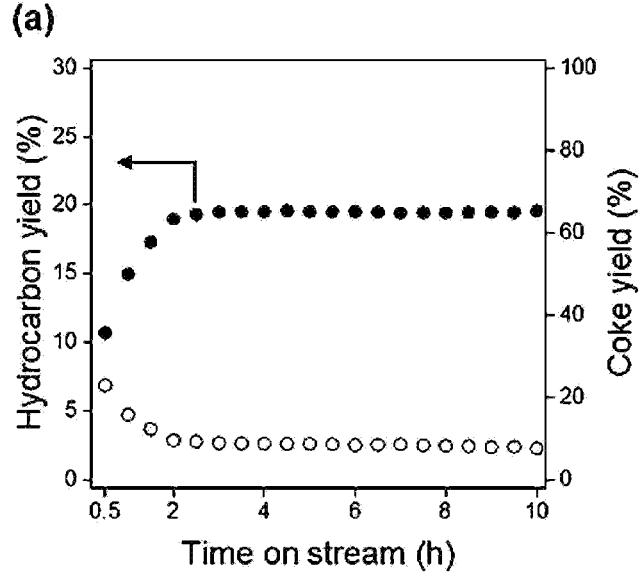
In FIG. 2, (a) and (b) are graphs illustrating a hydrocarbon yield and a coke yield in the non-oxidative direct methane conversion reactions performed according to Example 1 of the present disclosure and Comparative Example 1, respectively.
Figure 2:
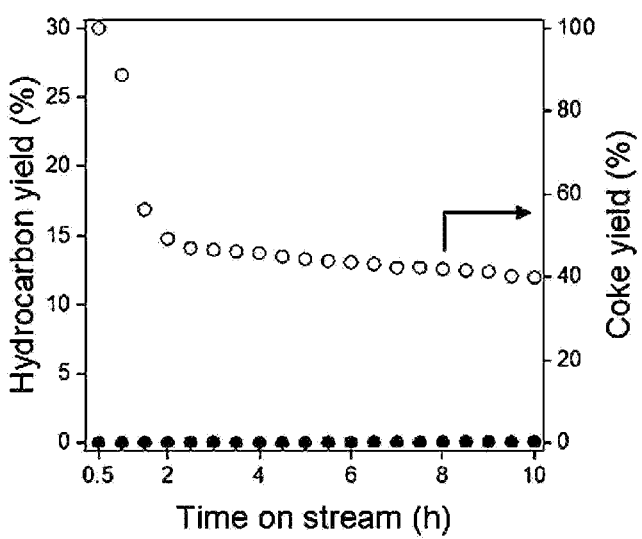

As illustrated in (b) of FIG. 1, the activation energy level for methane conversion is lower and the methane conversion rate is higher under the reaction conditions of Example 1 in which the superficial velocity is lower than that under the reaction conditions of Comparative Example 1. The results indicate that the conversion of methane on the surface of the Inconel 600 reactor is preferred under the conditions of Example 1.

[Experimental Example 2] Products of Non-Oxidative Conversion Reaction of Methane Direct conversion of methane was performed by supplying a methane feed gas in which methane and hydrogen are contained in a volume ratio of 1:4.4 into an Inconel 600 reactor. The superficial velocity of the feed gas was 133 cm·min$^{-1}$, the weight hourly space velocity of the gas was 8.9 min$^{-1}$, the gas retention time (gas phase) was 0.112 min, the reaction temperature was 1230° C., the reaction pressure $P_{total}$ was 1 bar, and the methane pressure $P_{CH4}$ was 0.44 bar. The conversion rate of methane, the yield of hydrocarbons, and the yield of coke over reaction time are shown in FIG. 2. In the case of Example 1, the reaction was more stabilized so that the coke yield was as low as 6.4% and the hydrocarbon yield was as high as 20.7% for a reaction time of 10 hours, compared to the reaction of Comparative Example 1 in which the superficial velocity was relatively high. On the other hand, in the case of Comparative Example 1, the hydrocarbon yield was lower than 0.15% and the coke yield was as high as 40% after the methane conversion. As shown in Table 1, under the reaction conditions of Example 1, a stable reactive activity was exhibited for 10 hours. In this case, the $C_2$ hydrocarbon selectivity was 58.2%, and the aromatic compound selectivity was about 18.2%. The selectivity of ethane, which is a $C_2$ product, was 7.6%, the selectivity of ethylene was 38.3%, and the selectivity of acetylene was 12.3%. The selectivity of benzene, which is an aromatic compound, was 14.3%, the selectivity of toluene was 0.2%, the selectivity of naphthalene was 1.6%, and the selectivity of alkyl aromatics was 2.1%. On the other hand, under the reaction conditions of Comparative Example 2, the coke selectivity was 99.7%. In conclusion, the reaction conditions of Example 1 were confirmed to lower the rate of excessive dehydrogenation of methane or the rate of condensation reaction of producing secondary products (acetylene, ethylene, and benzene) on the surface, thereby lowering the selectivity of coke.

reaction. In the case of Example 1 in which direct conversion of methane was performed at a relatively low superficial velocity, the ratio of crystalline carbon to amorphous carbon was 3.44, whereas in the case of Comparative Example 1 in which the reaction was performed at a relatively high superficial velocity, the ratio of crystalline carbon to amorphous carbon was 58.11. The results reveal that the uniform dispersion of a specific type of carbon is an important factor in non-oxidative conversion of methane into a yield of hydrocarbons.

All simple modifications or alterations of the embodiments may be readily practiced by those skilled in the art, and thus all such modifications or alterations will fall within the scope of the present disclosure.

TABLE 1

| | Reaction time (h) | Conversion rate (%) | Selectivity (C mol %) | | | | | | | | |
|---|---|---|---|---|---|---|---|---|---|---|---|
| | | | ethane | ethylene | acetylene | $C_3$-$C_4$ | benzene | toluene | naphthalene | Akyl aromatics | Coke |
| Example 1 | 10 | 27.1 | 7.6 | 38.3 | 12.3 | 0 | 14.3 | 0.2 | 1.6 | 2.1 | 23.6 |
| Comparative example 1 | 10 | 40.2 | 0 | 0 | 0 | 0 | 0.2 | 0 | 0.1 | 0 | 99.7 |

Figure 3:
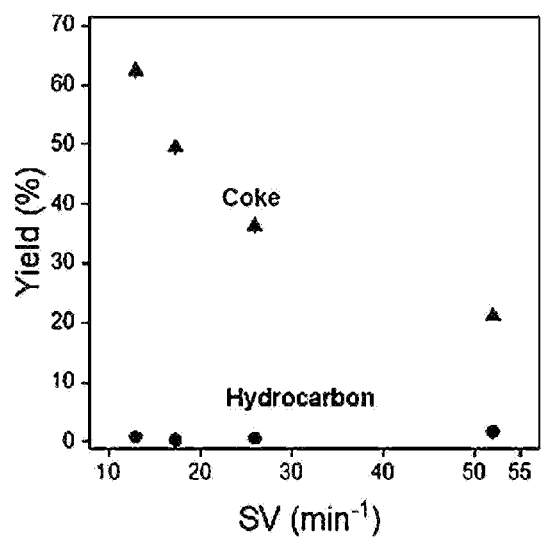
In FIG. 3, (a) is a graph illustrating changes in a product yield and a coke yield according to increase in weight hourly space velocity at a superficial velocity of 779 $cm \cdot min^{-1}$ and (b) is a graph illustrating changes in a product yield and a coke yield according to increase in superficial velocity at a weight hourly space velocity of 17.3 $min^{-1}$, according to the present disclosure.
Figure 3:
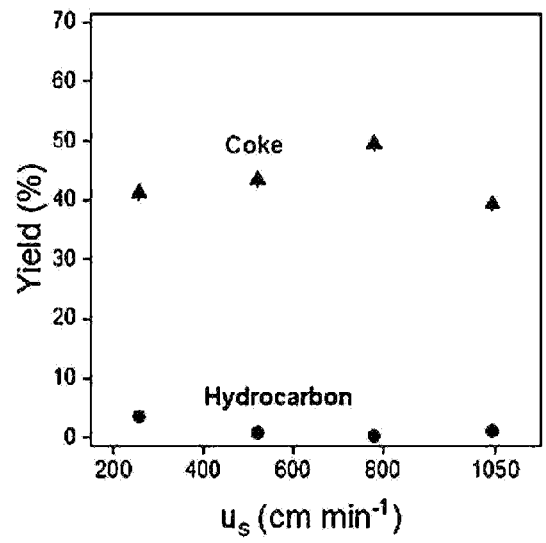

[Experimental Example 3] Reaction Activity According to Condition of Non-Oxidative Conversion Reaction of Methane Direct conversion of methane was performed using the same reactant composition in the same manner as in Experimental Example 2, except for the superficial velocity and the weight hourly space velocity. The results are shown in FIG. 3. In FIG. 3, (a) shows that when the superficial velocity is fixed to 779 cm·min$^{-1}$ and the weight hourly space velocity is increased to be 10 min$^{-1}$ or higher, the reaction activity of methane gradually decreases, and the hydrocarbon yield does not increase. In FIG. 3, (b) shows that when the weight hourly space velocity is fixed to 17.3 min$^{-1}$ and the superficial velocity is increased to 200 cm·min$^{-1}$, the hydrocarbon yield does not increase like the results of (a). These results reveal that the surface reaction of Inconel was promoted at a weight hourly space velocity of 10 min$^{-1}$ or higher and a space velocity of 200 cm·min$^{-1}$, and most of the methane was converted into coke.

Figure 4:
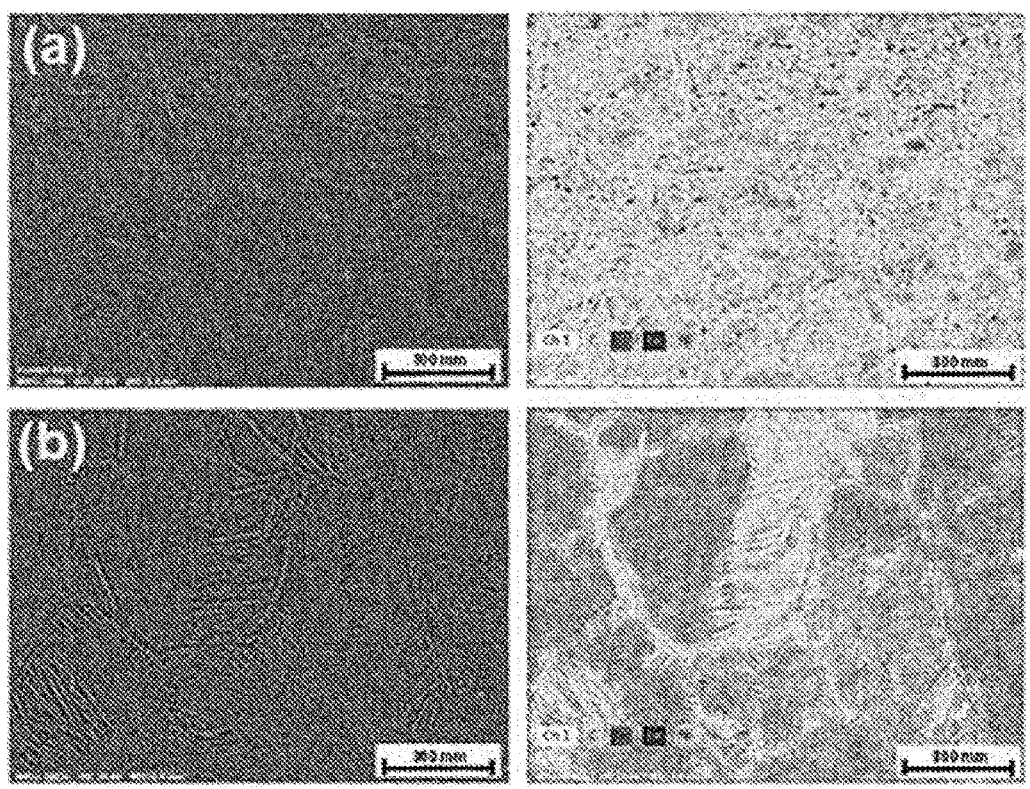
In FIG. 4, (a) and (b) illustrate SEM images and EDS results for an inner surface of an Inconel 600 reactor, which are measured after the non-oxidative direct methane conversion reactions performed according to Example 1 of the present disclosure and Comparative Example 1, respectively.
Figure 5:
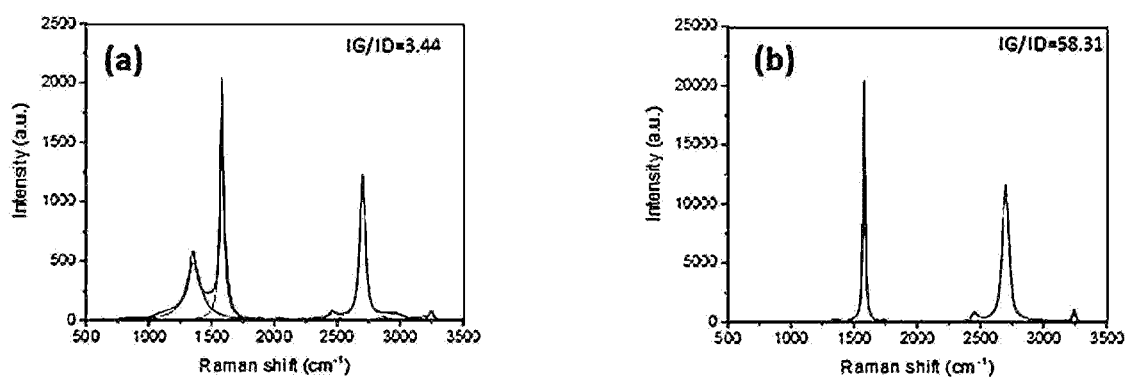
In FIG. 5, (a) and (b) illustrate Raman spectroscopy results for a carbon component in the inner surface of the Inconel 600 reactor, which are measured after the non-oxidative direct methane conversion reactions performed according to Example 1 of the present disclosure and Comparative Example 1, respectively.

[Experimental Example 4] Measurement of Concentration of Each Component in Inner Surface Layer of Inconel 600 Reactor FIG. 4 illustrates scanning electron microscope (JEOL, JS-6010) images of the inner surface layer of the Inconel 600 reactor for each of Example 1 and Comparative Example 1 of the present disclosure, and the results of energy disperse X-ray spectroscopy (EDS) for the inner same surface layers. As illustrated in (a) of FIG. 4, in the case where the methane feed gas is introduced into the Inconel 600 reactor at a relatively low superficial velocity, carbon atoms are uniformly dispersed in the reactor surface layer. However, when the methane feed gas is introduced into the Inconel 600 reactor at a relatively high superficial velocity, a metal film is formed on the inner surface of the reactor, and iron that promotes the formation of coke is precipitated, contributing to lowering the methane conversion rate.

In FIG. 4, the graph indicates the results of Raman spectroscopy to measure the content of crystalline carbon in the inner surface layer of the Inconel 600 reactor after the

The invention claimed is:

1. A method for non-oxidative direct conversion of methane, the method comprising:
   (a) supplying a methane feed gas comprising methane at a superficial velocity in a range of 100 cm·min$^{-1}$ to 200 cm·min$^{-1}$ to a reactor having an inner surface of made of Inconel 600; and
   (b) obtaining a compound having two or more carbon atoms, produced in the reactor having the inner surface made of Inconel 600.

2. The method of claim 1, wherein the methane feed gas is supplied at a weight hourly space velocity in a range of 8 min$^{-1}$ to 10.5 min$^{-1}$.

3. The method of claim 1, wherein the methane feed gas is supplied at a flow rate in a range of 80 cm$^3$ min$^{-1}$ to 300 cm$^3$·min$^{-1}$.

4. The method of claim 1, wherein the methane is comprised in the methane feed gas in an volume ratio 20% to 100% with respect to the volume of the methane feed gas.

5. The method of claim 1, wherein the methane feed gas comprises methane gas and hydrogen gas.

6. The method of claim 1, wherein a reaction was performed at a reaction temperature is in a range of 1000° C. to 1250° C.

7. The method of claim 1, wherein a ratio of amorphous carbon to crystalline carbon in a carbon layer formed in the Inconel 600 reactor is in a range of 1:4 to 2:3.

8. A non-oxidative direct methane conversion catalyst being a composite catalyst comprising Inconel 600 alloy coated with a carbon layer, wherein a ratio of amorphous carbon to crystalline carbon of carbon components is in a range of 1:4 to 2:3.

9. A method for non-oxidative direct conversion of methane, the method comprising: supplying a methane feed gas comprising methane gas and hydrogen gas to an Inconel 600 reactor having the catalyst of claim 8 on an inner surface thereof; and obtaining a compound having two or more carbon atoms, produced in the Inconel 600 reactor.

10. The method of claim 9, wherein the methane feed gas is supplied at a superficial velocity in a range of 100 cm·min$^{-1}$ to 200 cm·min$^{-1}$.

11. The method of claim 9, wherein the methane feed gas is supplied at a weight hourly space velocity in a range of 8 $\text{min}^{-1}$ to 10.5 $\text{min}^{-1}$.

\* \* \* \* \*